United States Patent
Gottlich (10) Patent No.: US 8,994,509 B2
(45) Date of Patent: Mar. 31, 2015

(54) METHOD FOR CONNECTING WIRELESS ELECTRIC ACTUATING DEVICES TO A MEDICAL APPLIANCE

(75) Inventor: Joachim Gottlich, Oberkochen (DE)

(73) Assignee: Carl Zeiss Meditec AG (DE)

( * ) Notice: Subject to any disclaimer, the term of this patent is extended or adjusted under 35 U.S.C. 154(b) by 963 days.

(21) Appl. No.: 12/202,547

(22) Filed: Sep. 2, 2008

(65) Prior Publication Data

US 2009/0058608 A1     Mar. 5, 2009

(30) Foreign Application Priority Data

Sep. 4, 2007    (DE) .................. 10 2007 042 389

(51) Int. Cl.
| | |
|---|---|
| H04Q 5/22 | (2006.01) |
| G05B 19/02 | (2006.01) |
| H04B 1/20 | (2006.01) |
| G08C 19/12 | (2006.01) |
| G05B 23/02 | (2006.01) |
| G08B 5/00 | (2006.01) |
| G08B 5/36 | (2006.01) |
| A61B 19/00 | (2006.01) |
| A61C 1/00 | (2006.01) |
| G08C 17/02 | (2006.01) |
| A61B 17/00 | (2006.01) |

(52) U.S. Cl.
CPC ............... A61B 19/52 (2013.01); A61B 19/44 (2013.01); A61C 1/0023 (2013.01); G08C 17/02 (2013.01); A61B 19/5223 (2013.01); *A61B 2017/00212* (2013.01); *A61B 2017/00221* (2013.01); *A61B 2017/00973* (2013.01); *A61B 2019/448* (2013.01); *G08C 2201/20* (2013.01)
USPC ...... 340/10.34; 340/4.31; 340/4.36; 340/4.42; 340/13.24; 340/3.41; 340/815.6; 340/815.66

(58) Field of Classification Search
CPC ................................... A61B 2562/22
USPC ............ 606/1; 340/10.1–10.6, 5.1–5.92, 340/4.1–4.62
See application file for complete search history.

(56) References Cited

U.S. PATENT DOCUMENTS

| | | | | |
|---|---|---|---|---|
| 5,881,102 | A * | 3/1999 | Samson | 375/222 |
| 6,074,388 | A * | 6/2000 | Tockweiler et al. | 606/34 |
| 6,369,693 | B1 * | 4/2002 | Gibson | 340/5.8 |
| 7,359,363 | B2 * | 4/2008 | Sakai | 370/338 |
| 7,468,670 | B2 * | 12/2008 | Liu et al. | 340/572.1 |

(Continued)

FOREIGN PATENT DOCUMENTS

| | | |
|---|---|---|
| DE | 102 21 179 A1 | 12/2003 |
| DE | 102 45 591 A1 | 4/2004 |

(Continued)

*Primary Examiner* — Steven Lim
*Assistant Examiner* — Muhammad Adnan
(74) *Attorney, Agent, or Firm* — Gerald E. Hespos; Michael J. Porco; Matthew T. Hespos (57) ABSTRACT

Method for connecting wireless electric actuating devices (2) to a medical appliance (1) via a wireless communication channel, having the steps of initiating the connection operation for a wireless electric actuating device (2) to a medical appliance (1) and performing a connection procedure, in which the actuating device (2) is assigned to the medical appliance (1), characterized in that the initiation of the connection operation is carried out from the medical appliance (1).

12 Claims, 5 Drawing Sheets

(56) References Cited

U.S. PATENT DOCUMENTS

| | | | |
|---|---|---|---|
| 7,691,097 B2* | 4/2010 | Miyazawa | 606/1 |
| 2002/0098835 A1* | 7/2002 | Flick | 455/420 |
| 2002/0156466 A1* | 10/2002 | Sakurai et al. | 606/1 |
| 2003/0149875 A1* | 8/2003 | Hosaka | 713/168 |
| 2003/0224729 A1* | 12/2003 | Arnold | 455/59 |
| 2005/0080403 A1* | 4/2005 | Takahashi | 606/1 |
| 2006/0047199 A1 | 3/2006 | Miyazawa | |
| 2006/0116667 A1* | 6/2006 | Hamel et al. | 606/1 |
| 2006/0219049 A1 | 10/2006 | Horvath et al. | |
| 2006/0255961 A1* | 11/2006 | Hofer et al. | 340/825.22 |
| 2007/0043339 A1 | 2/2007 | Horvath et al. | |
| 2007/0166662 A1 | 7/2007 | Lint et al. | |

FOREIGN PATENT DOCUMENTS

| | | |
|---|---|---|
| JP | 9-47459 | 2/1997 |
| JP | 2002-64418 | 2/2002 |
| JP | 2006-165831 | 6/2006 |
| JP | 2007-089119 | 4/2007 |
| WO | WO 9606499 A2 * | 2/1996 |
| WO | 9802860 | 1/1998 |
| WO | WO 9802860 A1 * | 1/1998 |
| WO | WO 03/094708 A1 | 11/2003 |
| WO | WO 2004/019751 A2 | 3/2004 |
| WO | WO 2005001790 A1 * | 1/2005 |
| WO | 2007047128 | 4/2007 |
| WO | WO 2007047128 A1 * | 4/2007 |

* cited by examiner

METHOD FOR CONNECTING WIRELESS ELECTRIC ACTUATING DEVICES TO A MEDICAL APPLIANCE

BACKGROUND OF THE INVENTION

1. Field of the Invention

The invention relates to a method for connecting wireless electric actuating devices to a medical appliance, such as an operation microscope.

2. Description of the Related Art

During an operation (OP), a large number of medical appliances can be used. These appliances can be used directly to operate, such as a laser, or assist the treating physician during the OP, such as an operation microscope. The operation of such medical appliances by an operating physician or an assistant is frequently carried out with the foot. The reason for this is, firstly, that the operating physician and the assistant as far as possible have their hands free to operate and do not have also to use them for adjusting the medical appliances. Secondly, operating elements of medical appliances are often difficult to sterilize, so that contact with the hand entails the risk of contamination.

If, in an operating theater, a footswitch unit (FSU) or another electric actuating device is used to control a medical appliance, for example to control the stand of an operation microscope, the corresponding appliance is intended to carry out only the function which is in particular initiated by this footswitch unit or in particular by this actuating device. This can be achieved by means of a cable-bound connection between the actuating device (in the following text, actuating device is to be understood to mean any type of operating element for the medical appliance, that is to say including a footswitch unit, for example). However, a cable connection has the disadvantage that, firstly, it can be associated with a trip hazard and, secondly, mobile medical appliances can become caught in cables. The risk therefore increases the more medical appliances and associated actuating devices are used in an operating theatre.

There are therefore endeavors to replace cable-bound actuating devices by wireless actuating devices, in which the communication between the actuating device and the medical appliance is carried out without cables, for example via radio signals, infrared signals, ultrasound signals, etc. If such wireless actuating devices are used to control a medical appliance, the corresponding stand should carry out only the functions which are initiated by an actuating device which has been assigned to the medical appliance previously by executing a specific connection procedure, or so-called "pairing". If functions were to be triggered by another actuating device located in the vicinity and belonging to another appliance, this could lead to complications.

A wireless footswitch unit for a medical treatment appliance is described in US 2007/166662 A1. In order to connect the footswitch unit, a synchronization pushbutton arranged on the footswitch unit is actuated and triggers a connection procedure to the medical appliance. During the connection procedure, identification addresses of the actuating device and of the medical appliance are exchanged.

A wireless actuating device for a medical appliance is likewise described in WO 2004/019751 A2. In this actuating device, the connection procedure is also triggered by the actuating device. As distinct from the footswitch unit in WO 2007/084668 A2, the connection procedure is not carried out via the actual wireless signal transmission path but via a second signal transmission path with a lower range, specifically provided for the connection procedure. In order to perform the connection procedure, the footswitch unit must therefore be brought close to the medical appliance since otherwise, because of the low range of the specific signal transmission path, the performance of the connection procedure would not be possible. As a result, the risk of an unintended connection to a wrong, further removed medical appliance is reduced.

As compared with this prior art, it is an object of the present invention to provide an advantageous connection method for connecting wireless electric actuating devices to a medical appliance via a wireless communication channel.

SUMMARY OF THE INVENTION

The method according to the invention for connecting wireless electric actuating devices to a medical appliance via a wireless communication channel comprises the steps of initiating the connection operation for a wireless electric actuating device to a medical appliance and performing a connection procedure, in which the actuating device is assigned to the medical appliance. In the method according to the invention, the initiation of the connection operation is carried out from the medical appliance.

The fact that the connection operation is initiated from the medical appliance and not by the actuating device, as is usual in the prior art, means that the initiative for the connection operation lies with the medical appliance. As a result, the actuating device can always be connected only precisely to the medical appliance which has initiated a connection operation. Other medical appliances which have not initiated any connection operation are not available to the connection operation, so that erroneous connections can be avoided.

If two or more medical appliances are used close by one another in such a way that their radio range overlaps during regular operation and a connection operation is initiated simultaneously by two medical appliances having overlapping ranges of the wireless communication channel, it is nevertheless possible for one actuating device to be connected to the wrong medical appliance. At this point, it should be mentioned that the connection operation is usually performed by the user actuating a pushbutton, and the user is therefore able to carry out the connection operations to the medical appliances one after another, so that an erroneous connection cannot be made. However, if simultaneous initiation of a connection operation is nevertheless carried out, erroneous connections can be avoided by the transmitter power of the medical appliance and/or of the actuating device being reduced during the connection operation. As a result of reducing the transmitter power, the transmission ranges overlapping in the case of a regular transmitter power of the wireless transmission channel cannot overlap any more following the reduction in the transmitter power. In particular, the transmitter power can be reduced to such an extent that communication between the medical appliance and the actuating device is possible only in the immediate near range.

In particular, the initiation of the connection operation can therefore trigger a reduction in the transmitter power of the transmitter of the medical appliance and a subsequent transmission of a request to perform the connection procedure with a reduced transmitter power. It is then possible for only those actuating devices which are located in the near range of the medical appliance to receive the request to perform the connection procedure. It is then in particular also possible to transmit a broadcast request as a request to perform the connection procedure.

Advantageously, following the reception of a request to perform the connection procedure by an actuating device, the transmitter power of the transmitter of the corresponding actuating device is reduced before the actuating device transmits an answer to the request and the connection procedure is carried out. As a result of lowering the transmitter power of the transmitter of the actuating device, an erroneous connection can be reliably avoided even when there is a second medical appliance, which likewise has initiated a connection operation and is within the transmitter range of the non-reduced transmitter power but not within the transmitter range of the reduced transmitter power. By means of suitable distances between an actuating device and the medical appliances and/or by means of a suitable level of reduction in the transmitter power, it is possible for the actuating device to be connected only to the closest medical appliance.

If the reduction in the transmitter power and in particular the answer to the request are made only when a connection is enabled by actuating an enable pushbutton on the actuating device, it is possible to avoid actuating devices which are located within the reduced transmitter range around the medical appliance but are not to be connected to the latter being wrongly connected to the medical appliance. Additionally or alternatively, it is possible for an already existing assignment of the actuating device to be canceled when the latter replies to the request. This measure prevents an actuating device from being able to be connected simultaneously to two medical appliances. As a result, there is always an unambiguous assignment of the actuating device to a specific medical appliance.

It is additionally advantageous if the connection operation is terminated by the medical appliance if no actuating device replies to the request from the medical appliance within a predefined time interval. Since, in this refinement of the method, the medical appliance does not remain permanently in the connection mode, a connection is no longer possible following the expiry of the predefined time interval. In the case of a plurality of medical appliances, connection operations can therefore be carried out in such a way that a connection operation to a further medical appliance is not initiated before the predefined time interval has elapsed. In this way, there is always only one medical appliance available for the connection operation, which permits erroneous connections to be avoided reliably.

During the connection procedure, that is to say following the transmission of the request by the medical appliance and the reply to the request by the actuating device, identification codes, for example the serial numbers of the appliances involved in the connection procedure, are exchanged. The identification codes can be stored in the medical appliance and/or in the actuating device in a nonvolatile memory. The assignment is then maintained in the corresponding medical appliance and the corresponding actuating device even if the appliance or the actuating device is switched off or the communication link is interrupted, for example because they are moved so far away from each other that they are no longer within the mutual transmitter range.

In order to permit the assignment of a plurality of actuating devices to a medical appliance, the assignment of actuating devices already connected to the medical appliance can be maintained in the medical appliance when a further actuating device is connected to the medical appliance. In this case, it is advantageous if the assignment of all the actuating devices connected to the medical appliance can be canceled in response to a cancel command. In this case, the identification codes are deleted from the memory of the medical appliance. Following the cancellation of all the assignments, there is then the possibility of setting up assignments again from new. The cancellation of the assignment can, however, also be carried out when the first actuating device to be connected within the context of the connection operation is connected. The assignment of the actuating devices is then maintained only until a new connection method is carried out.

Following the completion of the connection procedure, the transmitter power of the medical appliance and/or the actuating device is advantageously increased again to its standard value, so that the connected actuating device can also be used outside the near range of the medical appliance.

The method according to the invention is suitable in particular for connecting wireless electric actuating devices to medical stands, such as stands for operation microscopes. The actuating devices can in this case be constructed in particular as footswitch units.

Further features, properties and advantages of the present invention emerge from the following description of an exemplary embodiment, making reference to the appended figures.

DETAILED DESCRIPTION OF THE PREFERRED EMBODIMENTS

Figure 1:
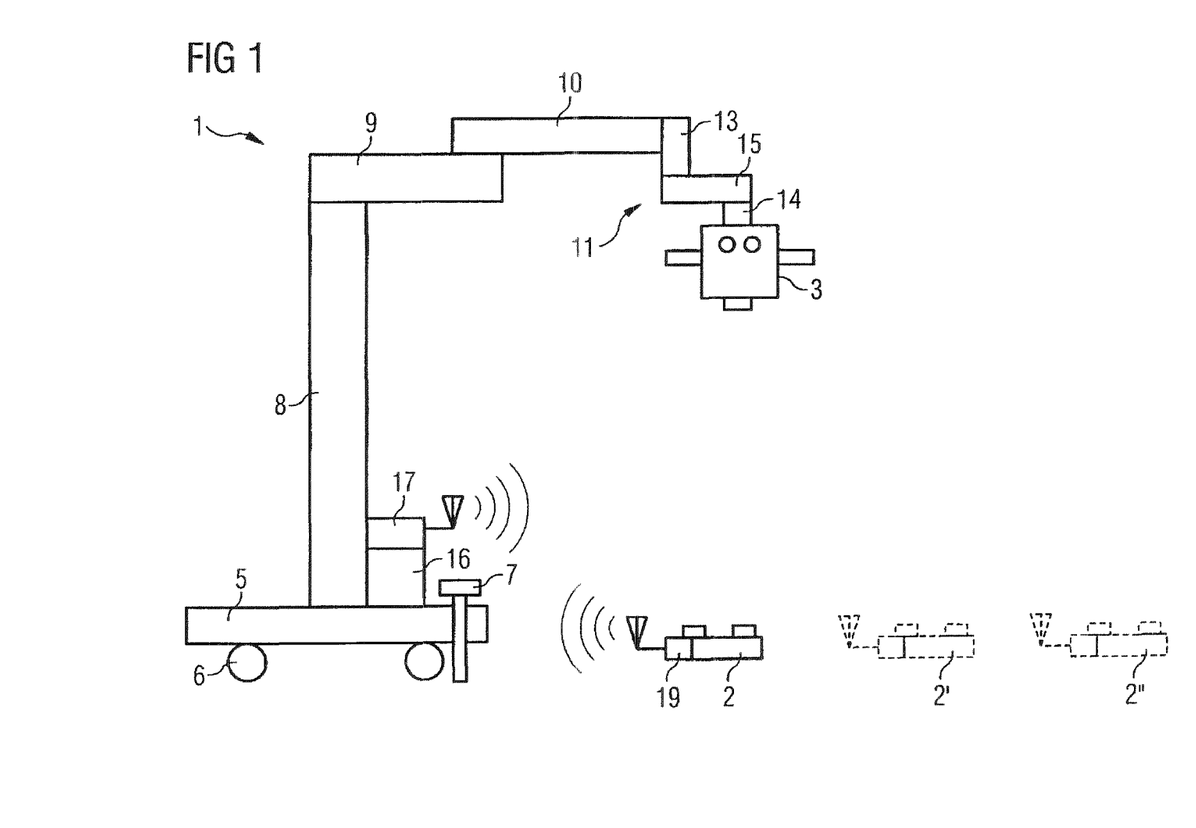
FIG. 1 shows a stand having a microscope mount and an operation microscope mounted thereon as an example of a medical appliance.

A stand 1 having a microscope 3 fixed thereto, which is an operation microscope here, is illustrated in FIG. 1 as an example of a medical appliance which is equipped with at least one wireless footswitch unit 2, for example based on Bluetooth, as an actuating device. The stand 1 rests on a stand base 5, on the underside of which there are rollers 6, which permit the stand 1 to be moved. In order to prevent unintentional movement of the stand 1, the stand base 5 additionally has a foot-operated brake 7.

Figure 2:
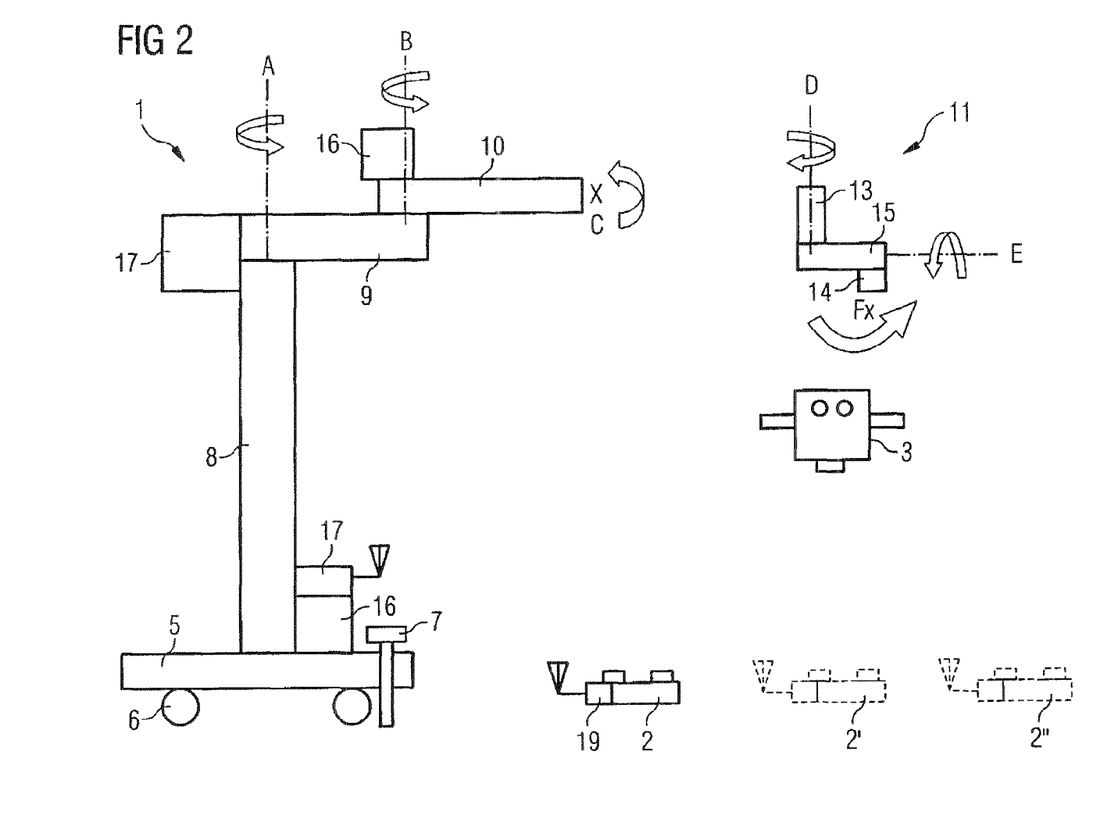
FIG. 2 shows the degrees of freedom provided by the stand and the mount from FIG. 1.

The actual stand 1 comprises as stand elements an adjustable-height stand column 8, a loadbearing arm 9, a spring arm 10 and a microscope suspension 11 which, in turn, comprises a connecting element 13, a swivel arm 15 and a holding arm 14. The degrees of freedom provided by the stand elements for positioning the operation microscope 3, and of which at least some can be controlled by the footswitch unit 2, are shown in FIG. 2. At one end, the loadbearing arm 9 is connected to the stand column 8 such that it can rotate about an axis A. At the other end of the loadbearing arm 9, one end of the spring arm 10 is fixed such that it can rotate about an axis B parallel to the axis A, so that the loadbearing arm 9 and the spring arm 10 form a jointed arm. The other end of the spring arm 10 is formed by a tilting mechanism (not illustrated), to which the microscope suspension 11 is fixed and which permits the microscope suspension 11 to be tilted about the axis C.

The microscope suspension 11 has an axis of rotation D, a swivel axis E and a tilt axis F, about which the microscope can be rotated, swiveled and tilted. Using a connecting element 13, the microscope suspension 11 is fixed to the outer end of the spring arm 10 such that it can rotate about the axis of rotation D. The axis of rotation D extends along the connecting element 13. The connecting element 13 is adjoined by a swivel arm 15, with the aid of which the microscope 3, more precisely a holding arm 14 fitted to the swivel arm 15 and to which the microscope 3 is fixed by means of a microscope mount (not illustrated), can be swiveled about the swivel axis E. The swivel axis E extends through the swivel arm 15. The angle between swivel arm 15 and connecting element 13, that is to say the angle between the swivel axis E and the axis of rotation D, can be varied by means of an adjusting mechanism arranged between the connecting part 13 and the swivel arm 15.

Through the holding arm 14, at right angles to the plane of the illustration, there runs the tilt axis F, which permits the operation microscope 3 to be tilted. The operation microscope 3 is fixed to the holding arm 14 by means of a microscope mount, not illustrated.

The degrees of freedom of the microscope suspension 11 and the possible adjustments of the operation microscope 3, for example focusing, acuity, magnification, etc., can likewise be adjusted via a wireless actuating element 2', 2". In this case, it is possible to provide an actuating device for the entire system comprising stand, mount and microscope or to provide individual actuating devices for individual appliances of the overall system, for example separate footswitch units for stand 1, mount 11 and microscope 3.

On the stand 1 there is additionally a control unit 16 for controlling the stand 1 and/or the mount 11 and/or the operation microscope 3. The control unit 16 is based on the same wireless transmission technology as the footswitch unit 2 and has a transmitter/receiver 17 which, in the present example, is Bluetooth-capable. The footswitch unit 2 also correspondingly has a Bluetooth-capable transmitter/receiver 19.

In order to prevent unintended displacement of the microscope 3 from a chosen position, the stand elements and the joints between the stand elements are provided with brakes (not illustrated), which are fixed after the positioning of the microscope 3. Suitable brakes are brakes to be actuated both manually and also electrically.

In order to ensure that the stand system with the operation microscope 3 accepts control commands only from the correct footswitch unit 2, the appropriate footswitch unit 2 must be connected to the stand system. If the stand 1, the mount 11 or the microscope 3 have a dedicated footswitch unit, separate connection operations have to be carried out for all three appliances.

The connection and assignment for example of a footswitch unit 2 or another actuating device to the stand 1 is carried out in a simple way for the user and can be performed in a secure manner. A precisely defined sequence, in which the transmitter power of the radio modules involved is reduced to a minimum in order to permit the assignment only in the near range, ensures that only an intended assignment (pairing) is possible. This assignment is then maintained until the next pairing operation. A stand executes only commands which received from an associated footswitch unit or another associated actuating device. Units assigned to each other can additionally be made visually distinguishable from one another by additionally applied color codes.

Figures 3, 3A:
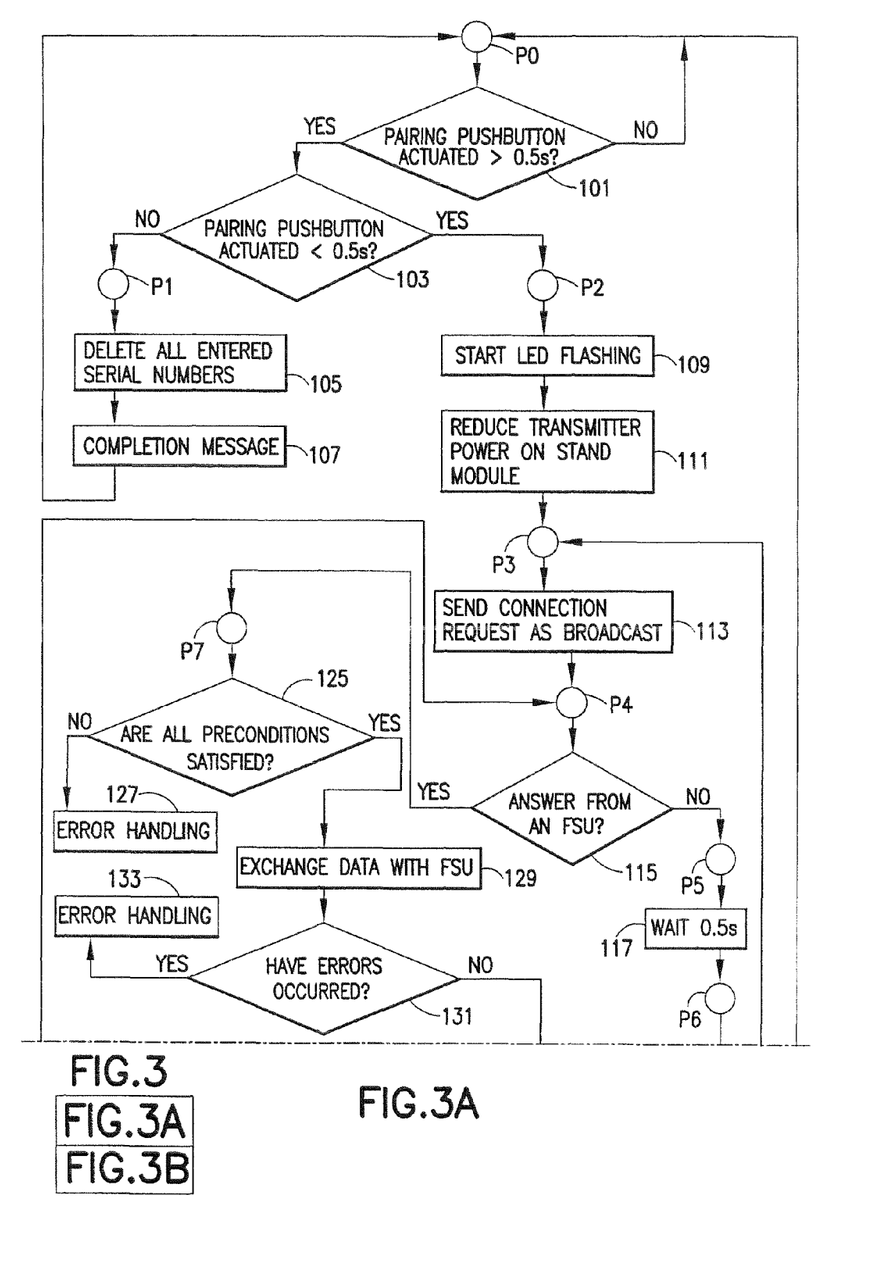
FIG. 3 shown a flow diagram which represents the method for connecting the wireless actuating device to the medical appliance from the side of the medical appliance.
Figure 3B:
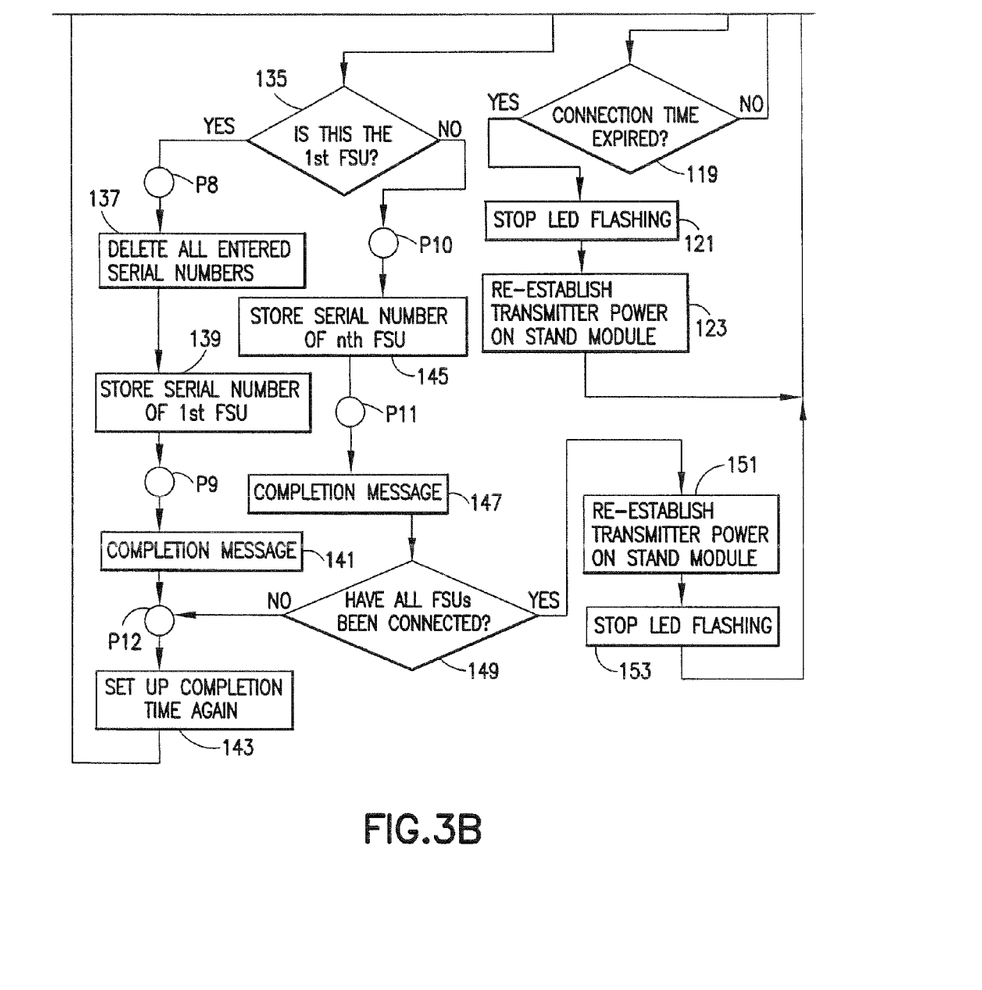
Figure 4:
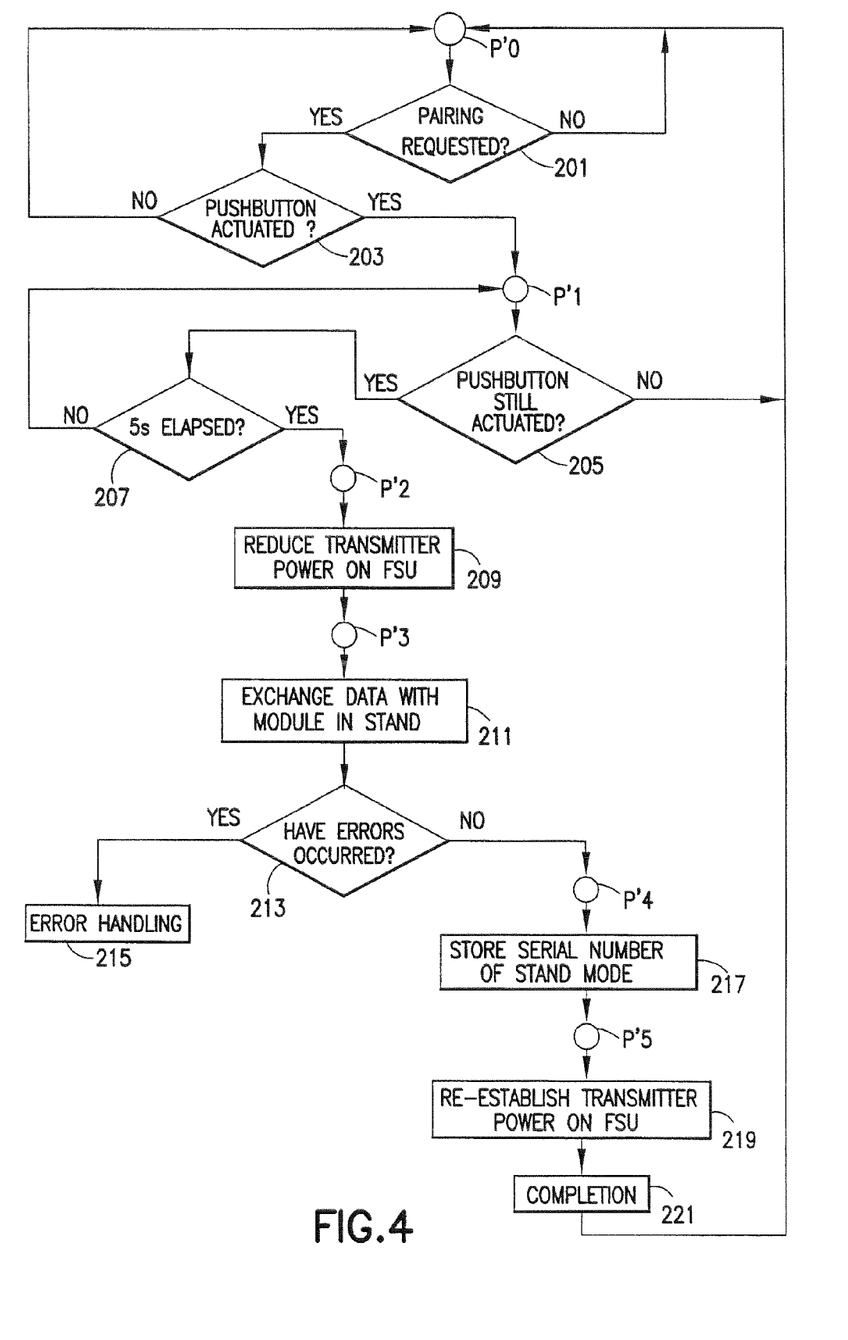
FIG. 4 shown a flow diagram which represents the method for connecting the wireless actuating device to the medical appliance from the side of the actuating device.

The progress of the connection method will be described below with reference to FIGS. 3 and 4, using the example of the connection of a footswitch unit 2 to the stand 1. In this case, FIG. 3 shows the part of the connection operation proceeding in the control system 16 of the stand, while FIG. 4 illustrates the part of the connection operation proceeding in the footswitch unit 2.

At the start of the connection method, the control unit 16 of the stand 1 is in process P0, which represents an idling process. If what is known as a pairing pushbutton is actuated in this state, the connection method for connecting the footswitch unit 2 to the stand 1, the so-called pairing, is initiated. In a first step 101 a query is then raised as to whether the pairing pushbutton has been actuated for longer than half a second. If the answer to this query is no, then the system remains in the idling process. If the answer to the query is yes, the method proceeds to step 103, in which a query is raised as to whether the pairing pushbutton has been actuated for less than five seconds. If the answer to this query is no, then the method changes to the cancellation process P1, in which in step 105 all the existing assignments of actuating devices 2 to the stand 1 are canceled, by all the serial numbers of actuating devices entered at the stand 1 being deleted. Following the output of a completion message in step 107, the control unit then returns to the idling process P0.

If in step 103 the query as to whether the pairing pushbutton has been actuated for less than five seconds is answered in the affirmative, the method proceeds to process P2, in which an LED display on the stand 1 is caused to flash in step 109 and the transmitter power of the transmitter 17 on the stand is reduced in step 111. The method then proceeds to process P3, in which in step 113 a request for connection to the stand 1 is sent. The processes P2 and P3 are used to initiate the connection operation and can be seen overall as an initiation process for the connection procedure.

Following the initiation of the connection operation, the method proceeds to process P4, which represents a waiting process, in which an answer from an actuating device, that is to say for example the footswitch unit 2, is awaited. If in step 115 of the waiting process P4 it is established that no answer from an actuating device has come in, the method proceeds to process P5, in which in step 117 a waiting time of half a second is allowed to elapse before the method proceeds to process P6. In process P6 a query is then raised as to whether a predefined time interval has expired (step 119), that is to say a predefined connection time period has expired. If the answer is in the negative, the method returns to process P3, in which the request for connection is transmitted again as a broadcast request. If, on the other hand, it is established in step 119 that the predefined time interval has expired, then the method proceeds to step 121, in which the flashing of the LED on the stand 1 is stopped, and then to step 123, in which the transmitter power of the transmitter 17 on the stand 1 is raised again to its initial value. After that, the method returns to the idling process P0.

If, on the other hand, it is established in step 115 that the footswitch unit 2 has answered the request for connection, the method proceeds to process P7. In process P7, first of all in step 125 a query is raised as to whether all the preconditions for the performance of the connection procedure have been satisfied. If the answer is in the negative, the method proceeds to step 127, in which error handling can be carried out. If, on the other hand, all the preconditions for the performance of the connection procedure have been satisfied, the process P7 proceeds to step 129, in which the control unit 16 of the stand 1 exchanges data with the footswitch unit 2. Within the context of this data exchange, the serial numbers are also exchanged between the footswitch unit 2 and the control unit 16 of the stand 1. The footswitch unit 2 is then assigned to the stand 1 by using the serial numbers exchanged. In step 131, a check is then made to see whether errors have occurred during the data exchange. If this is true, the process P7 proceeds to step 133, in which error handling can be carried out. If no errors have occurred, then in step 135 a request is raised as to whether the footswitch unit 2 is the first actuating device for which the connection procedure has been carried out. If this is true, then the method proceeds to process P8.

In process P8, in a first step (step 137), all the previously entered serial numbers are deleted and the serial number of the footswitch unit 2 is then stored in a nonvolatile memory (step 139). As a result of the storage in a nonvolatile memory, the serial number remains stored even if the Bluetooth connection between the footswitch unit 2 and the control unit 16 or the power supply of one of the two appliances is interrupted. As a result, the assignment is also maintained during a loss of the Bluetooth connection or the power supply. If the Bluetooth connection on the power supply is re-established, no renewed connection is therefore necessary, as distinct from the prior art.

Following the storage of the serial number, the method proceeds to process P9, in which in step 141 a completion message is output. After that, in a process P12, the predefined time interval for the answers to the broadcast request is set up again and the method returns to process P4, in which an answer to the broadcast request is awaited.

If it established in step 135 that an actuating device has already been connected to the stand 1 within the context of the connection method, the method proceeds to process P10 instead of to process P8, in which process P10 the serial number of the currently connected footswitch unit is stored as the Nth serial number, without deleting all the previously entered serial numbers (step 145). In a further process P11, a completion message (step 147) is then generated next and it is queried as to whether all the actuating devices have been connected (step 149). If this is not true, the method proceeds to the process 12, already described previously, in which the predefined time interval is set up again, before the method returns to process P4. If, on the other hand, it is established in step 149 that all the actuating devices have been connected, then the process P11 increases the transmitter power to its initial value in step 151, so that the original transmitter power, provided for regular operation, is established again. In step 153, the flashing of the LED is then canceled, and the method returns to the idling process P0.

With the connection of the last actuating device, the connection method has been completed.

Hitherto, with reference to FIG. 3, the processes proceeding in the control unit 16 of the stand 1 within the context of the connection method have been described. With reference to FIG. 4, the processes proceeding in the footswitch unit 2 during the connection process will now be described. In order to distinguish the processes proceeding in the footswitch unit 2 from the processes proceeding in the control unit 16, the processes proceeding in the footswitch unit 2 will in each case be designated as process P'.

At the start of the connection method, the footswitch unit 2 is in an idling process which, in FIG. 4, is designated process P'0. In this idling process, a query is raised at regular intervals as to whether a broadcast request relating to connection to the stand 1 has been transmitted by a medical appliance, by the stand 1 in the present exemplary embodiment (step 201). If such a broadcast request is not received, then the footswitch unit 2 remains in the idling process P'0. If, on the other hand, a broadcast request has been received, then the method proceeds to step 203, in which a query is raised as to whether an enable pushbutton on the footswitch unit 2 has been actuated. If this is not true, then the method remains in the idling process P'0. On the other hand, if the enable pushbutton has been actuated, the method proceeds to process P'1.

First of all, process P'1 raises a query as to whether the enable pushbutton is still actuated. If this is not true, then the method returns to the idling process P'0. If the enable pushbutton is still actuated, then in step 207 a query is raised as to whether five seconds have elapsed. If this is not true, then the method returns to the initial state of the process P'1, so that in step 205 a new query can be raised as to whether the enable pushbutton is still confirmed. In this way, the performance of the connection procedure is enabled only when the enable pushbutton has been actuated for at least five seconds. If this is not true, then it is established in step 205 that the pushbutton is no longer being actuated, so that the method returns to the idling process P'0. By means of the measure that the enable pushbutton must be actuated for at least five seconds, it is possible to avoid unintended connection of the footswitch unit 2 to a medical appliance as a result of inadvertent activation of the enable pushbutton, which is generally not carried out over a time period of five seconds.

If the enable pushbutton has been actuated for longer than five seconds, then in process P'2 the transmitter power of the footswitch unit 2 is reduced to such an extent that the transmitted signal can be received only in its near range (step 209). After that, the method proceeds to process P'3. Process P'3 carries out the actual connection procedure, in which data is exchanged with the control unit 16 of the stand 1. Within the context of this data exchange, the serial numbers of the stand and its control unit 16 and the footswitch unit 2 are exchanged as identification codes. After the data has been exchanged in step 211, a check is made in step 213 as to whether errors have occurred. If this is the case, then process P'3 proceeds to an error handling state 215, in which it is possible to check what errors have occurred and which permits error rectification.

If, on the other hand, no errors are detected during the data exchange in step 213, then the method proceeds to process P'4, in which the serial number of the stand and/or of its control unit 16 are stored in a nonvolatile memory. The advantages of the storage in the nonvolatile memory have already been described with reference to the process P8, which proceeds in the control unit 16 of the stand 1 during the connection method.

After the serial number of the stand and/or of its control unit 16 have been stored in step 217, the connection method proceeds to process P'5, in which the transmitter power of the footswitch unit 2 is raised again to its original value provided for regular operation (step 219). After that, in step 221, a completion message is output before the method returns to the idling process P'0.

For the footswitch unit 2, the connection method has therefore been completed. The connection method is also completed in the control unit 16 when it has been established there in step 149 that all the actuating devices have been connected. On the other hand, if all the actuating devices have not yet been connected, then the connection method continues to be carried on by the control unit 16 until all the actuating devices have been connected.

After the connection method has been completed both in the footswitch unit 2 and on the stand 1, regular operation can be started. During each transmission of data, the stored identification codes, that is to say the stored serial numbers in the present exemplary embodiment, are also transmitted as an address in order that the transmitter and receiver of the data can be identified.

In the connection method according to the invention, an assignment is maintained until a new connection method is carried out, all the previously entered serial numbers then being deleted in the stand 1 in the process P8. By means of the process P1, however, all the serial numbers can also be deleted without carrying out an actual connection procedure, so that all the assignments to the appropriate medical appliance are canceled without new assignments being set up.

The fact that the duration of the broadcast request transmitted cyclically in the processes P3 and P4 is time-limited means that the probability that an actuating device will inadvertently be connected to a medical appliance is limited. In addition, as the result of reducing the transmitter power to a low power stage, only those actuating devices which are in the immediate vicinity of the medical appliance making the call for connection are addressed. The flashing code of the LED additionally provides the user with information that the corresponding appliance is in the connection method.

In addition, as distinct from the prior art, the connection method within the context of the invention is not initiated by the actuating device 2 but by the control unit 16 of the medical appliance. A connection of the actuating device 2 can therefore be made only to such a medical appliance as has initiated a connection method. On the other hand, other medical appliances are not available to the actuating device for the performance of a connection method. In addition, the probability of an erroneous connection can thereby be reduced.

Furthermore, an assignment of an actuating device to a medical appliance does not have to be repeated before a new connection operation is initiated. Because of the nonvolatile storage of the identification codes, the assignment is specifically maintained even if the power supply to the medical appliance and/or to the actuating device is interrupted or if the wireless communication link is interrupted. The assignment is canceled only when a new connection operation is carried out or the cancellation of the assignment is brought about deliberately by actuating a pushbutton. A user therefore does not have to start a new connection procedure each time the medical appliance is switched on, each time a battery is changed, etc. or each time the communication was interrupted briefly.

Overall, as a result of the method according to the invention, when a plurality of actuating devices is used in the immediate vicinity of a medical appliance, the danger that the latter will be assigned an erroneous actuating device is reduced as compared with the prior art.

What is claimed is:

1. A method for connecting a wireless electric actuating device that has a transmitter/receiver to a medical appliance that has a transmitter/receiver via a wireless communication channel, the method comprising the steps:
determining by the medical appliance whether a connection operation for the wireless electric actuating device has been initiated by a user and, if it is determined that a connection operation has been initiated, reducing power of the transmitter/receiver of the medical appliance to a reduced medical appliance power level and then transmitting from the medical appliance at the reduced transmitter/receiver power level, a request to perform the connection operation, or, if it is determined that a connection operation has not been initiated, returning to an idling process;
determining by the actuating device whether a request to perform the connection operation has been received, and, if it has been determined that a request to perform the connection operation has been received, reducing transmitter power of the transmitter/receiver of the actuating device to a reduced actuating device power level and then transmitting from the actuating device at the reduced actuating device power level an answer to the request from the medical appliance and assigning the actuating device to the medical appliance, or, if it is determined that a pairing request has not been received, returning to the idling process.

2. The method of claim 1, characterized in that the request to perform the connection procedure is a broadcast request.

3. The method of claim 1, characterized in that the assignment of actuating devices already connected to the medical appliance is maintained in the medical appliance when a further actuating device is connected to the medical appliance.

4. The method of claim 3, characterized in that the assignment of all the actuating devices connected to the medical appliance is canceled in the medical appliance in response to a cancel command.

5. The method of claim 1, wherein the assigning step includes exchanging identification codes of the medical appliance and/or the actuating device during the connection procedure.

6. The method of claim 5, wherein the respective identification codes are stored in the medical appliance and/or in the actuating device in a nonvolatile memory.

7. The method of claim 1, further comprising cancelling an existing assignment of actuating devices in the medical appliance when an answer is received by the medical appliance.

8. The method of claim 1, further comprising terminating the connection operation by the medical appliance if no actuating device replies to the request from the medical appliance within a predefined time interval.

9. The method of claim 1, wherein, following the completion of the connection procedure, increasing the transmitter power of the medical appliance and/or the actuating device to a regular operating value.

10. The method of claim 1, wherein the connection is enabled by actuating an enabling pushbutton on the actuating device.

11. The method of claim 1, wherein the reduction in the transmitter power and the answer to the request are made by the actuating device only when a connection is enabled by a user of the actuating device.

12. A method for connecting a wireless electric actuating device that has a transmitter/receiver to a medical appliance that has a transmitter/receiver via a wireless communication channel, the method comprising the steps:
determining by the medical appliance that is in an idling process whether a pairing pushbutton of the medical appliance has been actuated to initiate a connection operation for connecting the wireless electric actuating device to the medical appliance, and, if it is determined that a connection operation has been initiated, reducing power of the transmitter/receiver of the medical appliance to a reduced medical appliance power level and then transmitting from the medical appliance at the reduced transmitter/receiver power level, a broadcast request to perform the connection operation, or, if it is determined that a pairing pushbutton of the medical appliance has not been actuated, returning to the idling process;
determining by the actuating device that is in an idling process whether a request for performing a connection operation has been received, and, if it is determined that a request for performing a connection operation has been received, determining whether an enabling pushbutton is actuated, or, if it is determined that a pairing request has not been received, returning to the idling process; and
in response to receiving a request for performing a connection operation, reducing transmitter power of the transmitter/receiver of the actuating device to a reduced actuating device power level and then transmitting from the actuating device at the reduced actuating device power level an answer to the request from the medical appliance and assigning the actuating device to the medical appliance if it is determined that the enabling pushbutton is actuated, or, if it is determined that the enabling pushbutton is not actuated, returning to the idling process.

* * * * *